United States Patent [19]
Duarte

[11] Patent Number: 5,255,069
[45] Date of Patent: Oct. 19, 1993

[54] ELECTRO-OPTICAL INTERFEROMETRIC MICRODENSITOMETER SYSTEM

[75] Inventor: Francisco J. Duarte, Rochester, N.Y.

[73] Assignee: Eastman Kodak Company, Rochester, N.Y.

[21] Appl. No.: 829,366

[22] Filed: Feb. 3, 1992

Related U.S. Application Data

[63] Continuation-in-part of Ser. No. 735,205, Jul. 24, 1991, abandoned, which is a continuation of Ser. No. 373,954, Jun. 30, 1989, abandoned.

[51] Int. Cl.$^5$ .............................................. G01B 9/02
[52] U.S. Cl. ..................................... 356/354; 356/345; 356/443
[58] Field of Search ................ 356/353, 354, 361, 443, 356/445, 345

[56] References Cited

U.S. PATENT DOCUMENTS 4,068,956  1/1978  Taboada .............................. 356/443

OTHER PUBLICATIONS

"Dispersion Theory of Multiple-Prism Beam Expanders for Pulsed Dye Lasers", Duarte et al, Optics Communications, Nov. 1982, 303–307.

"Measurement of Film-Grain Noise by Coherent Scattering", Yu et al, Optik, May 1974, 167–172.

*Primary Examiner*—Samuel A. Turner
*Attorney, Agent, or Firm*—Robert L. Randall

[57] ABSTRACT

There is disclosed an interferometric system including electro-optical apparatus and method for examining and characterizing ultra fine details of various specimens such as a piece of photographic film. The method includes illuminating a specimen with a thin wide substantially pure Gaussian light beam, detecting the interfering patterns of light from the specimen, and characterizing ultra fine details of elements of the specimen by means of the detected light patterns. The apparatus includes a laser, a magnifying telescope, a multi-prism beam expander, and a linear array of photo-diodes. Signals from the photo-diodes are displayed on an optical multichannel analyzer (OMA) to provide a waveform characteristic of ultra fine elements of the specimen. Both "near-field" and "far-field" characterizations are possible and details of elements having diameters of the order of the wavelength of the light used (e.g., about 0.6 μm) are detected.

32 Claims, 13 Drawing Sheets

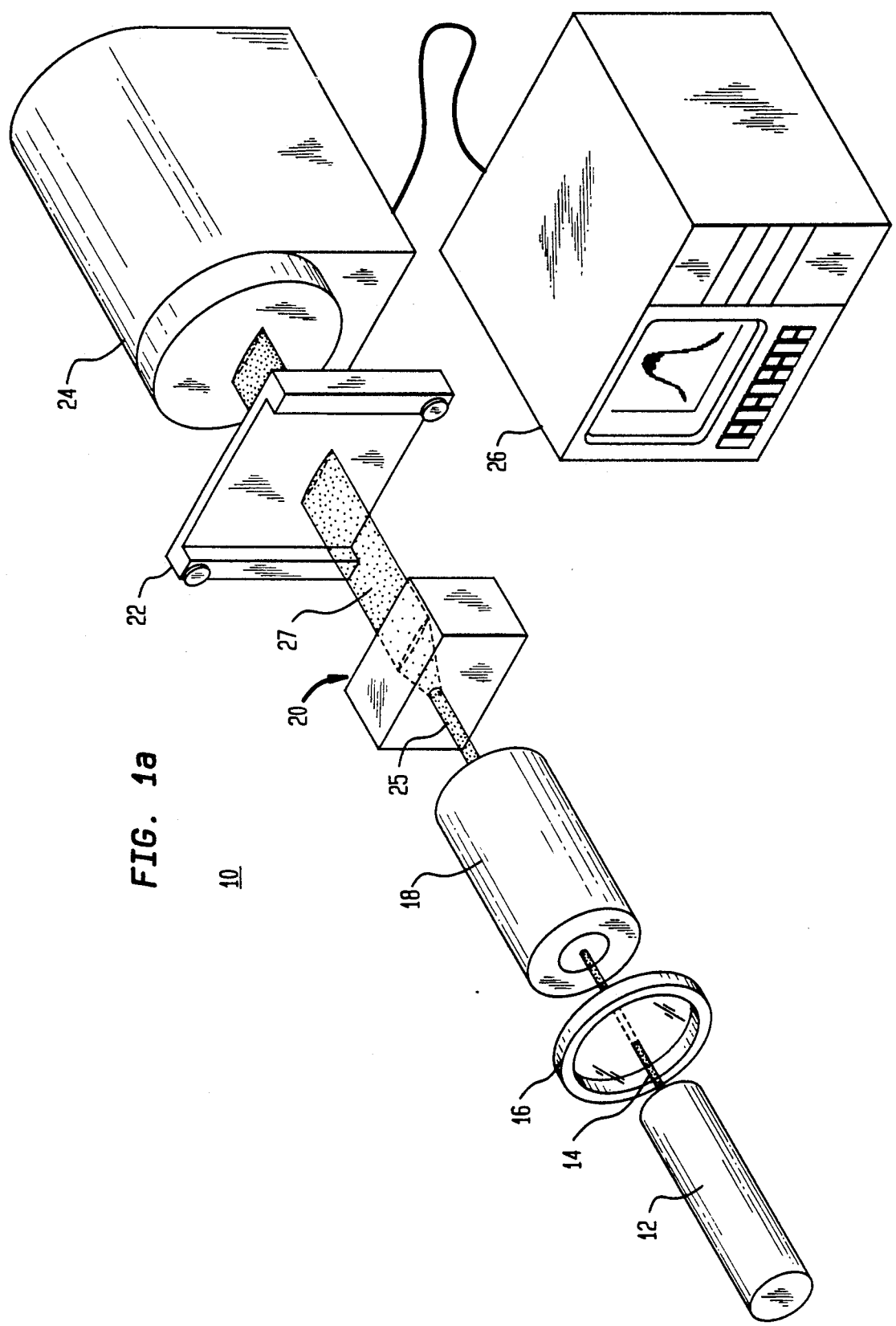

ELECTRO-OPTICAL INTERFEROMETRIC MICRODENSITOMETER SYSTEM

The present patent application is a continuation-in-part of U.S. patent application, Ser. No. 735,205, filed Jul. 24, 1991, now abandoned, which is a continuation of U.S. patent application, Ser. No. 373,954, filed Jun. 30, 1989, now abandoned, both in the name of the present inventor, and having an assignee in common with the present patent application.

FIELD OF THE INVENTION

This invention relates to an interferometric system comprising electro-optical apparatus and method employing the principles of quantum mechanics and the interference of light waves in examining and characterizing ultra fine details of various objects, such as a piece of photographic film.

BACKGROUND OF THE INVENTION

A conventional microdensitometer uses a light source to illuminate an object or specimen being examined. Light from the source is shined through the specimen and detected by an electronic sensor (typically, a photo-multiplier) which in the conventional manner is located quite close to the specimen. This is termed "near-field" examination, in contrast to "far-field" where interferometric effects predominate, as will be explained hereinafter. The intensity of the transmitted light from the specimen is measured electronically and provides an indication of the density of one or several fine details of the specimen (such as a "grain" of photographic film). By making a multitude of individual measurements over the area of the specimen, a statistical analysis of the density and graininess of the specimen is obtained. A fuller discussion of the principles, analysis and evaluation of photographic-type imaging processes is given in the book entitled "Image Science", by Dainty and Shaw, published by Academic Press, 1974, (see particularly pages 39, 285 and 286). Another analysis of microdensitometer results is given in the book "The Theory of the Photographic Process", fourth edition, by T. H. James, published by the Eastman Kodak Co., 1977, (see particularly p. 619).

One limitation of a conventional microdensitometer is its very narrow depth of focus (typically less than a small fraction of a millimeter). This in turn limits such apparatus to examining elements of a specimen lying in a very thin layer. But a specimen, such as a piece of photographic film, may actually have important elements of its structure (including the film substrate) at depths far beyond the focused plane of view of the microdensitometer apparatus. And, of course, the unfocused details of these elements cannot be easily characterized, if at all. Another, and more important limitation of a conventional microdensitometer is the fact that the details of an ultra small element of a specimen, such as a micron size "grain" of photographic film, cannot be distinguished by a conventional microdensitometer which uses optical apertures that are typically several dozens of microns in diameter. The use of high resolution photo-diode detectors does not enhance resolution in a conventional microdensitometer. Even the most advanced state-of-the-art semiconductor photo-diodes, having a diameter of only 3 microns, cannot properly determine the details of an element (as distinguished from merely detecting the presence or absence of the element) less than about 12 microns in diameter. In other words, to adequately characterize in "near-field" examination the details of an ultra small element of a specimen, the element should be large enough in diameter that, for example, four or more photo-detectors can span its diameter.

In addition to the limitations described above, a conventional microdensitometer apparatus has very limited dynamic range and very limited viewing diameter (e.g., 48 microns "spot" size).

It is highly desirable therefore to provide an electro-optical apparatus and method which can detect and characterize the details of ultra fine elements very much smaller in diameter, over a very much larger region of a specimen, with very much greater depth of focus, and with greater dynamic range than apparatus or method according to the prior art.

SUMMARY OF THE INVENTION

In accordance with the present invention there is provided an interferometric system including electro-optical apparatus and method employing the principles of quantum mechanics and the interference of light waves in examining optically and quantatively characterizing ultra small elements of a specimen, such as a piece of photographic film.

In accordance with a method provided by the invention a substantially pure Gaussian beam from a light source (such as a laser beam of suitable wavelength) is considerably magnified (for example, by about 20 power). The magnified beam is greatly spread or expanded laterally in one dimension (by a multiple-prism beam expander) into a wide, thin substantially pure Gaussian beam of light. This wide, thin Gaussian light beam is then shined through a specimen being examined. Light from the specimen is directed onto an electro-optical detector, such as a linear array of a thousand or more very small semi-conductor photo-diodes, which have a combined width approximately equal to the width of the light beam (e.g., a width about 25 mm). The detector is normally located a considerable distance (e.g., centimeters) from the specimen. The electronic signals from the detector are then processed in an optical multichannel analyzer (OMA) to obtain an interferometric characterization of many details of ultra fine elements lying in line along a length of the specimen. The interferometric light pattern, as seen by the detector and displayed on the OMA is a "far-field" pattern. As will be explained hereinafter the interferometric pattern can, if desired, be transformed using the principles of quantum mechanics into a computer display simulating an equivalent "near-field" pattern of individual details of elements of the specimen. This transformed, or "de-interfered" pattern is able to "show" ultra fine details of elements of the specimen even though these elements are very much smaller in diameter than the diameter of an individual photo-diode of the detector. Details of elements having diameters of the order of the wavelength of the light employed (e.g., about 0.6 micron) can be detected and characterized by this new method. Both "far-field" and "near-field" examination of a specimen can be employed, as will be explained hereinafter.

An electro-optical apparatus embodying the invention comprises a laser, a magnifying telescope, a multiple-prism beam expander, and a linear array of photo-diodes. An expanded light beam from the beam expander is passed through a specimen and the resulting pattern of light interference is detected by the photo-diode array. There are, for example, 1024 photo-diodes in the array, each about 25 microns in width. An optical multichannel analyzer (OMA) then processes the signals from the diode array to obtain a characterization of details of numerous fine elements of the specimen. An extended length of the specimen can thus be characterized at one time contrary to conventional apparatus where the light beam is scanned step-by-step along the sample a small spot at a time. Additional advantages provided by the present invention are far greater depth of focus, much greater sensitivity, much faster data collection, superior dynamic range, and much more compact size compared to prior-art apparatus.

Viewed from another aspect, the present invention is directed to apparatus comprising means for generating a Gaussian beam of light having a thickness which is substantially smaller than the width thereof, means for directing the beam of light so as to cause it to impinge upon an object whose physical characteristics are to be determined, and detector means for directing interferometric light waves from the object and for generating electrical signals representative of the physical structure of the object.

A better understanding of the invention, together with its important advantages will best be gained from a study of the following description given in conjunction with the accompanying drawings and claims.

BRIEF DESCRIPTION OF THE DRAWINGS

FIG. 1a is a perspective view in schematic form of an electro-optical apparatus in accordance with the present invention;

DETAILED DESCRIPTION

Figure 1B:
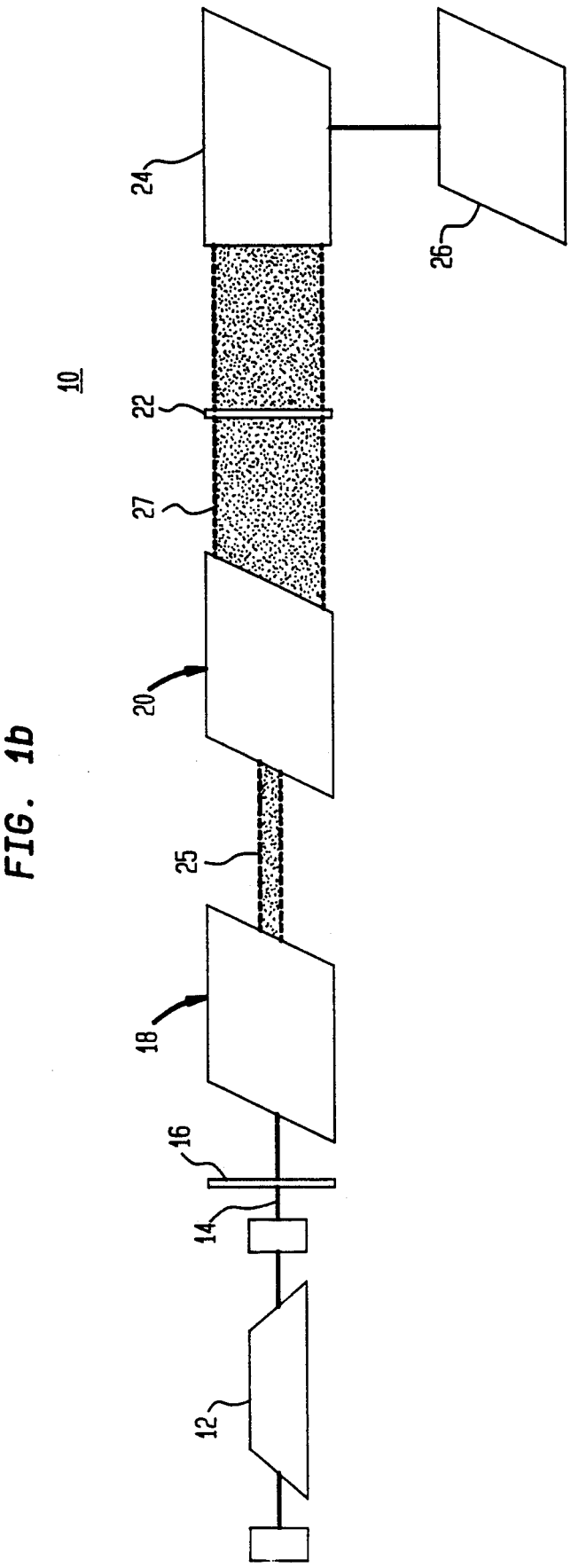
FIG. 1b is a schematic diagram of the electro-optical apparatus of FIG. 1a in accordance with the present invention.

With reference to FIGS. 1a and 1b, there is shown in schematic form, an electro-optical apparatus 10 constructed in accordance with the present invention. Apparatus 10 comprises a light source 12 which projects a beam along an optical axis 14. Light source 12 can be, for example, a two mW (2 mW) He-Ne laser ($\lambda = 632.8$ nm) which provides a p-polarized single transverse mode ($TM_{00}$) substantially pure Gaussian beam with a beam diameter of 0.5 mm. Alternatively, a 1000 mW Kr+ laser can be used. This laser emits in several transitions in the blue-red region of the spectrum at wavelengths of 476.2 nm, 482.5 nm, 520.8 nm, 530.9 nm, 568.2 nm, and 647.1 nm.

Figure 2:
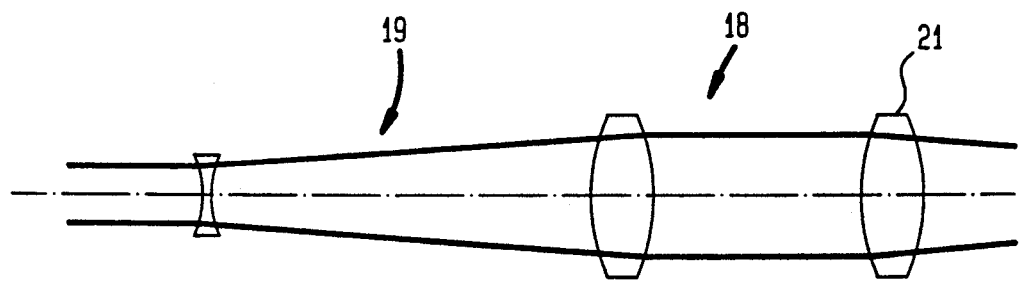
FIG. 2 is a schematic diagram of beam shaping optics of the apparatus of the present invention.

A beam from source 12 passes through a neutral density filter 16 and is projected onto beam-shaping optics 18 which, as shown in FIG. 2, include a telescope 19 and a convex lens 21. The telescope 19 is shown as Galilean, but it can also be newtonian. Telescope 19 provides a two-dimensional magnification factor of about twenty (20). Convex lens 21 can have a focal length of 40 cm.

The beam from optics 18, indicated at 25, is generally circular and passes through a one-dimensional multiple-prism beam expander 20. The beam from expander 20, indicated at 27, is a narrow and elongated substantially pure Gaussian and is directed onto a sample 22, for example, a photographic film. Light which passes through the sample 22 is intercepted by a detector 24. Detector 24 comprises a linear array of photosensitive elements (not shown here), for example, a photo-diode array composed of 1024 diodes or of 2048 diodes, each of which is 25 $\mu$m (micron) wide. Signals from detector 24 are delivered to a signal processor 26 which can include, for example, a CRT display. The functions of detector 24 and signal processor 26 can be provided, for example, by an EG&G Optical Multichannel Analyzer, No. 1460-D OMA III, having a 1463 detector module and 1420 detector.

Figure 3A:
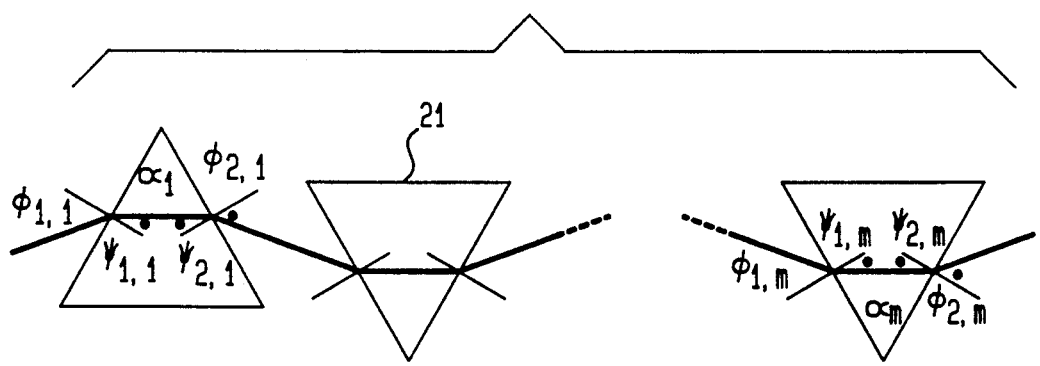
FIGS. 3a and 3b are schematic diagrams illustrating the multiple-prism beam expander used in the present invention.

An important feature of the present invention is the use of multiple-prism beam expander 20 to provide one-dimensional beam magnification. A series of prisms 21 are shown in FIG. 3a, and for a generalized multiple-prism array, the single-pass cumulative dispersion following the mth prism is given by the equation $$\left(\frac{d\phi_{2,m}}{d\lambda}\right) = \frac{\sin\psi_{2,m}}{\cos\phi_{2,m}} \frac{dn_m}{d\lambda} + \frac{\cos\psi_{2,m}}{\cos\phi_{2,m}} \frac{\cos\phi_{1,m}}{\cos\psi_{1,m}} \left[\frac{\sin\psi_{1,m}}{\cos\phi_{1,m}} \frac{dn_m}{d\lambda} \pm \frac{d\phi_{2,(m-1)}}{d\lambda}\right] \quad \text{Eq. (1)}$$

where the incidence angle $\phi_{1,m}$ and refraction angle $\Psi_{1,m}$ are related by Snell's law: $\sin \phi_{1,m} = n(\lambda) \sin \Psi_{1,m}$, where $n(\lambda)$ is the index of refraction of the prism material. This is a general equation applicable to prismatic arrays of any geometry or material. A more complete explanation of the derivation of equation (1) can be found in a paper, entitled "Dispersion Theory of Multiple-Prism Beam Expanders For Pulsed Dye Lasers", by Duarte and Piper, Opt. Commun. 43, 303 (1982). A full discussion is also given in Chapter 4 of the book "Dye Laser Principles", edited by Duarte and Hillman, and published by Academic Press, 1990. (See particularly Equation 4.21 on page 150, and pages 151 et.seq.).

Figure 3B:
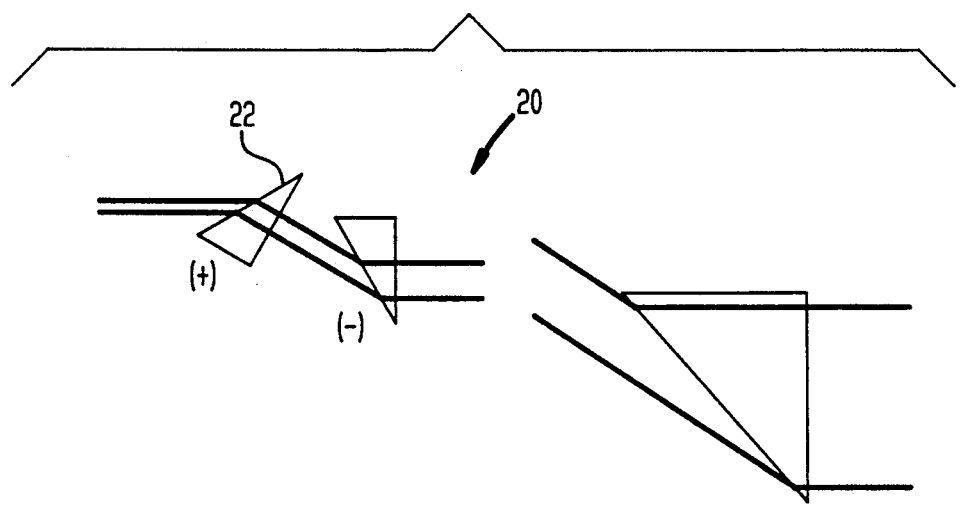

In a preferred embodiment of the multiple beam expander 20, right-angle prisms 22 of identical material are used, as shown in FIG. 3b. The plus (+) sign indicates an additive prism, and the minus (−) sign indicates a compensating prism. Prisms 22 are arranged for orthogonal beam exit (that is, $\phi_{2,m} = \Psi_{2,m} = 0$). In such a case the dispersion for an assembly of r prisms is given explicitly by the equation $$(d\phi_{2,r}/d\lambda) = \left( \prod_{j=1}^{r} k_{1,j} \right)^{-1} \sum_{m=1}^{r} (\pm 1) \left( \prod_{j=1}^{m} k_{1,j} \right) \tan\psi_{1,m}(dn/d\lambda) \quad \text{Eq. (2)}$$

where $k_{1,j}$, the individual beam expansion coefficient = (cos $\Psi_{1,j}$/cos $\phi_{1,j}$), and the overall beam expansion factor can be shown to be $$M = \prod_{j=1}^{r} k_{1,j}$$

For achromaticity, or zero dispersion, at the selected wavelength, the condition to be satisfied is $(d\phi_{2,r}/d\lambda) = 0$. Using the above equations, a number of alternative zero-dispersion beam expanders can be designed. Table I includes the necessary parameters for three different achromatic arrays, the first beam expander being composed of two prisms, the second of three, and the third of four. The material utilized in each of the prisms is quartz, and the selected wavelength is 647.1 nm (corresponding to a Kr+ laser transition) for which n = 1.45674. In interpreting Table I it should be noted that, for orthogonal exit designs, the apex angle of the prism $\alpha_m$ is equal to the corresponding refraction angle $\Psi_{1,m}$ which can be obtained by using sin $\phi_{1,m} = n_{(\lambda)}$ sin $\Psi_{1,m}$.

TABLE I

| | Basic Parameters for Three Zero-Dispersion Multiple-Prism Expanders | | | | |
|---|---|---|---|---|---|
| r | M | $\phi_{1,1}$ | $\phi_{1,2}$ | $\phi_{1,3}$ | $\phi_{1,4}$ |
| 2 | 3.54 | 73.14° | 51.77° | | |
| 3 | 5.29 | 64.08° | 64.08° | 60.65° | |
| 4 | 5.75 | 55.53° | 55.53° | 55.53° | 65.13° |

The double-prism expander (r=2) in Table I has an overall magnification factor of 3.54 (M=$k_{1,1}k_{1,2}$=[2.6] [1.36]). This expander is arranged in a compensating configuration of the (+, −) type. Since the incident beam on the beam expander 20 has a diameter of 10 mm, the one-dimensional Gaussian has a width of ~35 mm. The hypotenuse of the first prism can be 25 mm, and the hypotenuse of the second prism can be 50 mm.

In order to accommodate a photo-diode array having, for example, 2048 photo-diodes (50.80 mm wide), it is desirable to have expanders with more than two prisms. In line two of Table I, parameters are given for a three-prism compensating configuration of the (+, +, −) type with the first two prisms being identical, with $k_{1,1} = k_{1,2} = 1.8$ so that the overall magnification (M=$k_{1,1}$ $k_{1,2}$ $k_{1,3}$) becomes 5.29 when $k_{1,3}$=1.63. The expansion of a 10 mm diameter incident beam can be accomplished by prisms in which the hypotenuse for the first two prisms is 45 mm and the corresponding hypotenuse of the third prism is 70 mm. In line three of Table I, parameters are given for a four-prism expander arranged in the (+, +, +, −) compensating configuration. The first three prisms are identical with $k_{1,1} = k_{1,2} = k_{1,3} = n$ (that is, 1.45674). The fourth prism provides $k_{1,4} = 1.86$, thus allowing the overall magnification to become M=5.75. The hypotenuse for the first three prisms can be made equal to 45 mm and the last prism can have a hypotenuse of 70 mm.

Using Eq. (2), it can be shown that all of the arrangements in Table I provide $d\phi_{2,r}/d\lambda = 0$ for quartz at 647.1 nm. There is also very little angular deviation at the other end of the spectrum. For the blue transition of the Kr+ laser at 476.2 nm, it can be shown that the angular deviation for the double-prism expander becomes 0.0015°; for this angular deviation, a 10 cm distance can be translated into a displacement of 2.69 $\mu$m. For a photo-diode array having a resolution of, for example, 25 $\mu$m, a displacement of 2.69 $\mu$m is far too small to be detected.

A further advantage of the use of achromatic multiple-prism beam expanders is the drastic reduction in the beam deviations due to thermal variations. This can be easily illustrated since the thermal angular deviation factor is written as $$(d\phi_{2,r}/dT) = (d\phi_{2,r}/d\lambda)(dn/d\lambda)^{-1}(dn/dT) \quad \text{Eq. (3)}$$

From equation (3), it is apparent that an achromatic expander (for which we require $(d\phi_{2,r}/d\lambda) = 0$) minimizes thermal variations.

Transmission losses incurred in the multiple prism beam expander 20 can be found using the following recursion formula (equation)

$$L_m = L_{m-1} + (1 - L_{m-1})\,l_m \quad \text{Eq. (4)}$$

where $L_m$ is the cumulative loss at the mth prism, and the individual loss, for p-polarization, at that prism is given by the Fresnel formula $$l_m = \tan^2(\phi_{1,m} - \Psi_{1,m})/\tan^2(\phi_{1,m} + \Psi_{1,m}). \quad \text{Eq. (5)}$$

Using equations (4) and (5), the overall transmission for p-polarized light of the third expander (r=4, M=5.75) can be shown to be 90.87% when antireflection coatings are used for the exit faces of the prisms.

Figure 4:
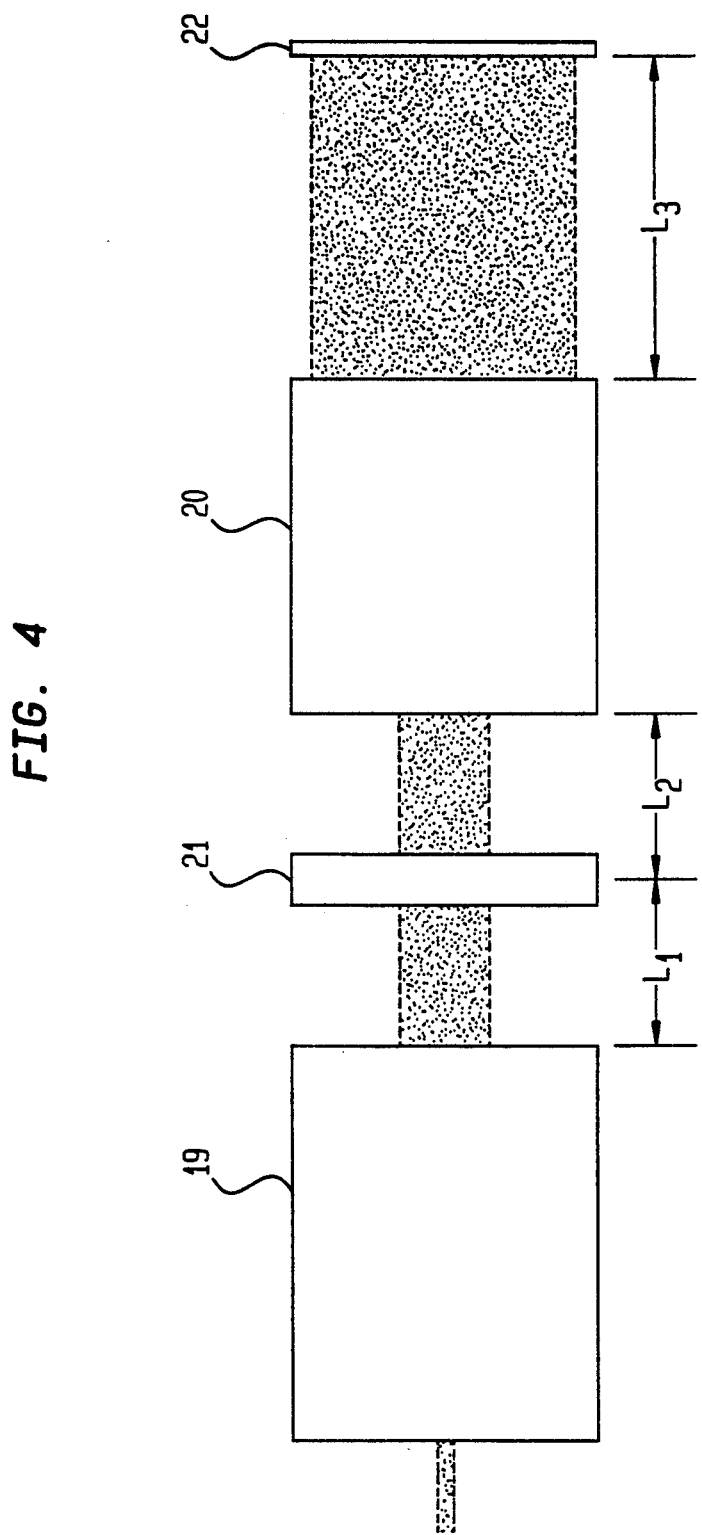
FIG. 4 is a schematic diagram showing certain elements of the apparatus of the present invention and the effect of beam expander thereof on a laser beam.

The optical physics which governs beam propagation in the present invention can be shown with reference to FIG. 3 which includes the different parameters of interest. For horizontal propagation the ray matrix of a multiple-prism expander composed of r prisms is given by $$\begin{bmatrix} A & B \\ C & D \end{bmatrix} = \begin{bmatrix} \prod_{m=1}^{r} k_m \ (\ell/n) \begin{bmatrix} \prod_{m=1}^{r} k_m \sum_{m=1}^{r} \left( \prod_{j=1}^{m} k_j \right)^{-2} \end{bmatrix} + \begin{bmatrix} \prod_{m=1}^{r} k_m \sum_{m=1}^{r-1} \left( \prod_{j=1}^{m} k_j \right)^{-2} \end{bmatrix} D \\ 0 & \left( \prod_{m}^{r} k_m \right)^{-1} \end{bmatrix} \quad \text{Eq. (6)}$$

where is the path at the prism, D the prism separation (assumed to be uniform), and n is the refractive index. Thus the overall ray transfer matrix is given by the equation $$\begin{bmatrix} M_t[M - (\zeta/f)] & B_t[M - (\zeta/f)] + \\ & (L_1 M/M_t) + (\zeta/M_t)[1 - (L_1/f)] \\ -M_t/(Mf) & (MM_t)^{-1}[1 - (L_1/f)] - [B_t/(Mf)] \end{bmatrix} \quad \text{Eq. (7)}$$

where $L_1$, $L_2$ and $L_3$ are defined in FIG. 4, B and $B_t$ are the corresponding upper right terms of the transfer matrices for the prism expander and the telescope, f is the lens focal length and $$\zeta = M L_2 + B + (L_3/M). \quad \text{Eq.(8)}$$

To find the width of the Gaussian beam we now use
$$w(B') = w_0[(A')^2 + (B'/L_R)^2]^{\frac{1}{2}} \quad \text{Eq.(9)}$$

where the A' and B' terms are given in Eq. (7) and $L_R$ is the Rayleigh length ($\pi w_0^2/\lambda$). For the vertical component the corresponding ray transfer matrix becomes $$\begin{bmatrix} M_t[1 - (L'_2/f)] & [1 - (L'_2/f)][B_t + (L_1/M_t)] + (L'_2/M_t) \\ -(M_t/f) & M_t^{-1}[1 - (L_1/f)] - (B_t/f) \end{bmatrix} \quad \text{Eq. (10)}$$

where $L_2$ is the optical path distance between lens 21 and the sample 22 (FIG. 4). For example, using parameter values applicable to apparatus 10, Equations (7)–(10) can be used to show that a 0.5 mm $TM_{00}$ beam from a He-Ne laser becomes 53.40 mm wide by 32.26 μm high at the focal plane (for $M = 5.75$ and $M_t = 20$). The beam height is the maximum value at the center of the Gaussian. The depth of focus of the Gaussian beam in this configuration is greater than 2000 μm. For these parameters the height and width of the elongated Gaussian have been verified experimentally.

Figure 5:
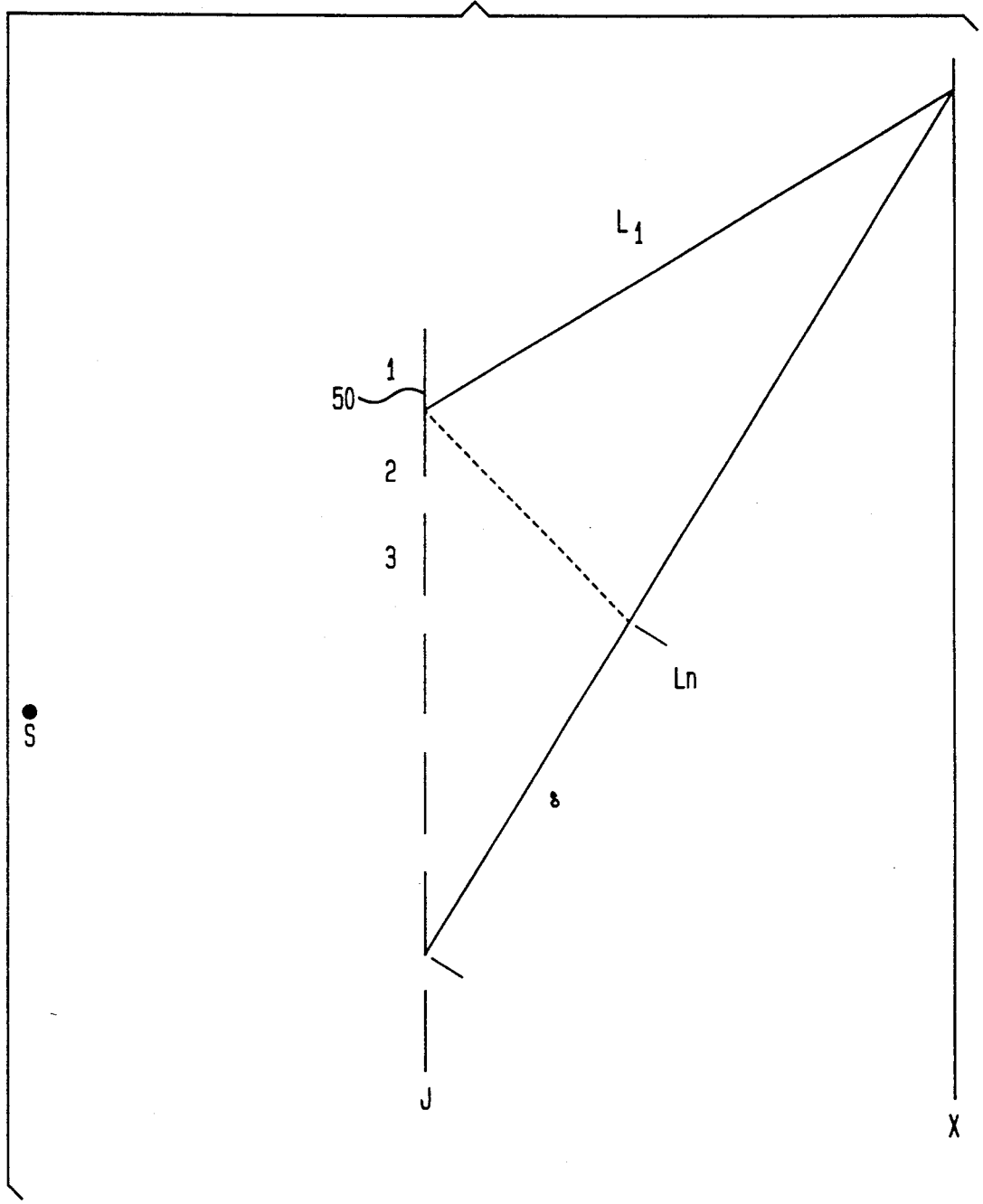
FIG. 5 is a diagram for use in explaining the interference pattern produced from a sample being evaluated.

A basic concept utilized in the present invention is the interpretation of the radiation-matter interaction as a one-dimensional coherent illumination of a row of slits. In practice, this concept can be translated into a row of wave functions whose amplitude is determined by the different transmission characteristics. The observed information is due to the collective interaction of these wave functions in the form of interference. The concept can be illustrated using an array of variable-width slits 50, as shown in FIG. 5, and this is directly applicable to the case of an N slit transmission grating or to a single-grain layer film. Using Dirac's notation, the probability amplitude for a photon to go from s to x (see FIG. 5) can be written as $$<x|s> = \sum_{j=1}^{N} <x|j><j|s>. \quad \text{Eq. (11)}$$

where $<j|s> = \Psi_{s,j} e^{-i\theta_j}$ and $<x|j> = \Psi_{x,j} e^{-i\phi_j}$. In these probability amplitudes, the quantities $\Psi_{s,j}$ and $\Psi_{x,j}$ may be assumed to take the form of a diffraction wave function or other appropriate distribution. Now, if $\Psi_j = \Psi_{s,j} \Psi_{x,j}$ and $\Omega_j = (\phi_j + \theta_j)$, then $$<x|s> = \sum_{j=1}^{N} \psi_j e^{-i\Omega_j}. \quad \text{Eq. (12)}$$

Hence, using the result $\cos \Omega = (\frac{1}{2})(e^{-i\Omega} + e^{i\Omega})$ it can be shown that the probability that a photon from s will reach 23 a plane x (FIG. 5) is given by the equation $$|<x|s>|^2 = \sum_{j=1}^{N} \psi_j^2 + 2 \sum_{j=1}^{N} \psi_j \left( \sum_{m=j+1}^{N} \psi_m \cos(\Omega_m - \Omega_j) \right). \quad \text{Eq. (13)}$$

Equation 13 is a generalized equation applicable to any one-dimensional N-slit interference problem. To simplify the description, it can be assumed that the probability amplitude for a photon to reach the single row of apertures from the source is the same for all slits 50, so that $$<1|s> = <2|s> = <3|s> = \ldots = <N|s> = \Psi_s e^{-i\theta}.$$

For this case of uniform illumination, the general equation is reduced to $$|<x/s>|^2 = \quad \text{Eq. (14)}$$

$$\psi_s^2 \left[ \sum_{j=1}^{N} \psi_{x,j}^2 + 2 \sum_{j=1}^{N} \psi_{x,j} \left( \sum_{m=j+1}^{N} \psi_{x,m} \cos(\phi_m - \phi_j) \right) \right].$$

Figure 6A:
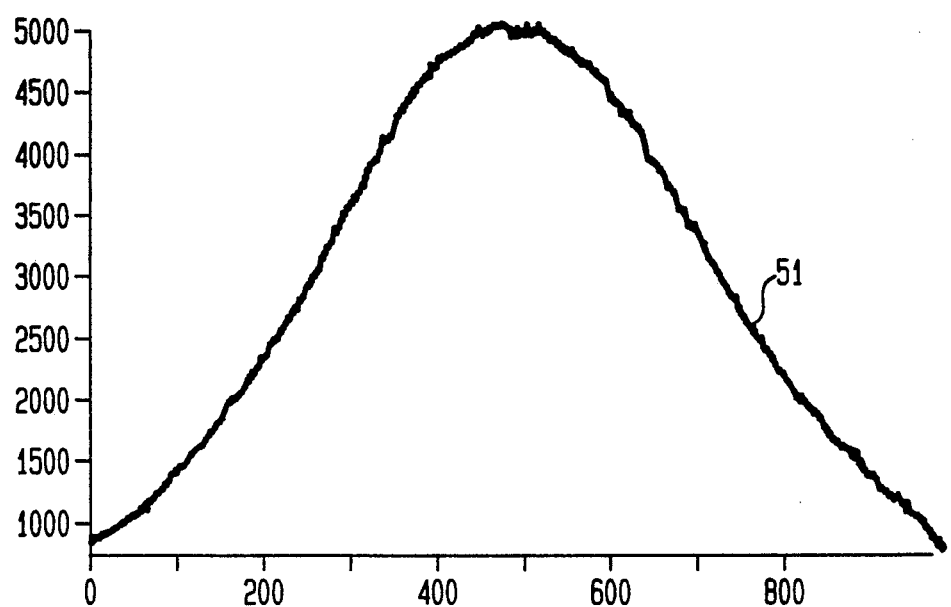
FIGS. 6a, 6b, and 6c show signal patterns produced by the apparatus of the present invention.
Figure 6B:
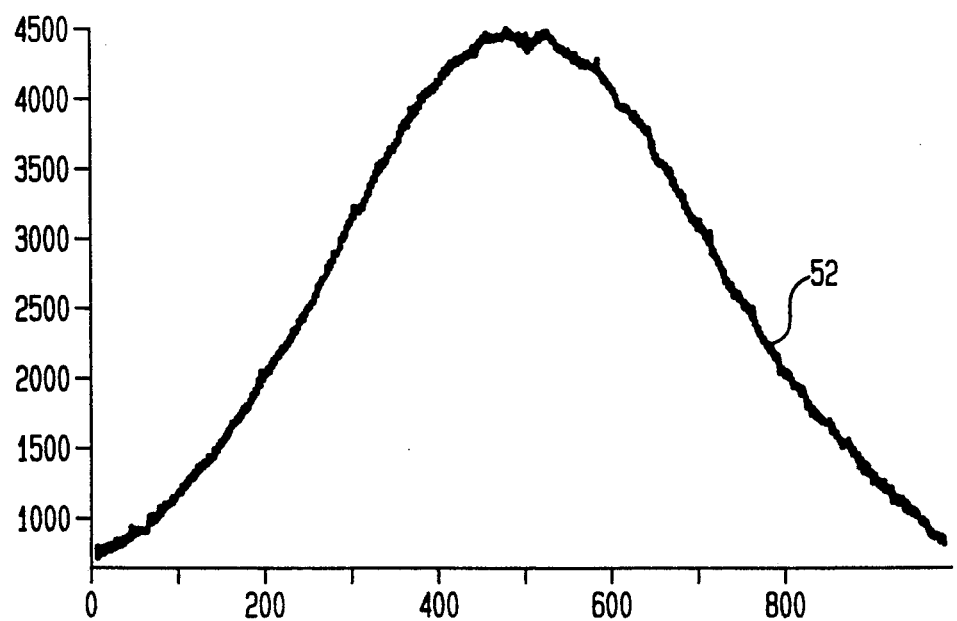
Figure 6C:
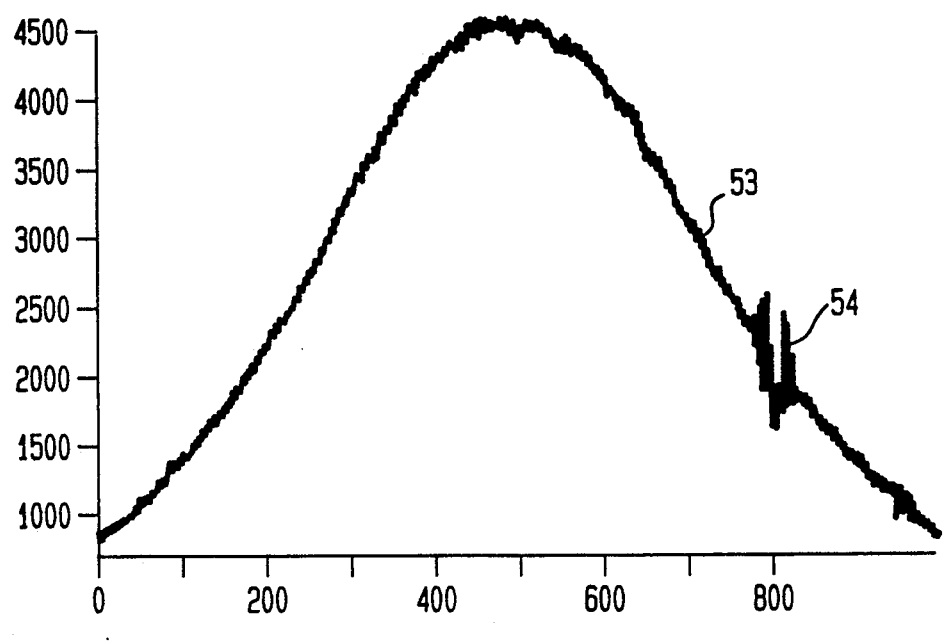
Figure 7A:
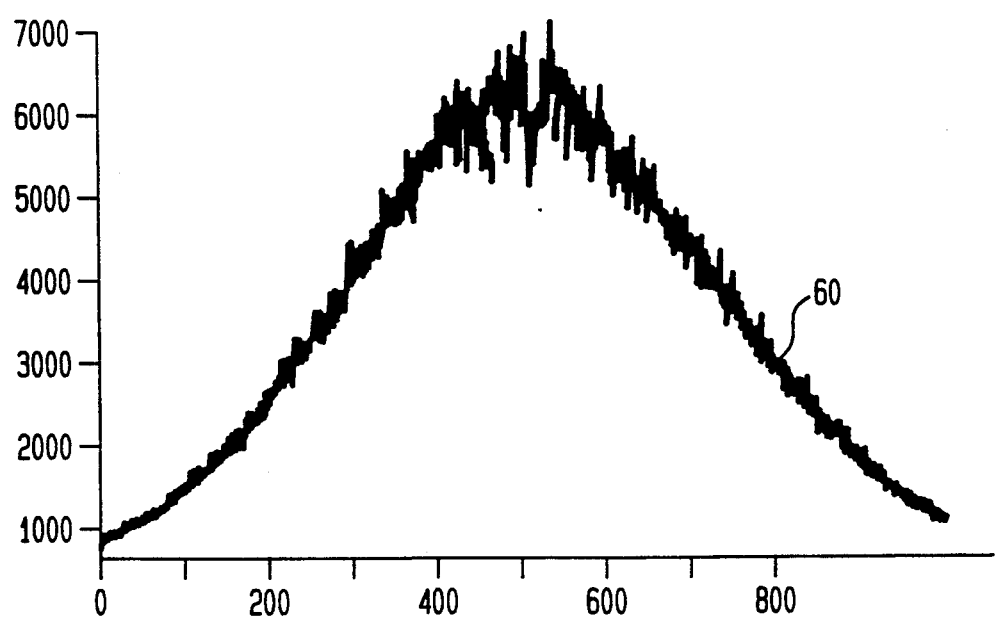
FIGS. 7a, 7b and 7c show interference patterns obtained from a black-and-white film.
Figure 7B:
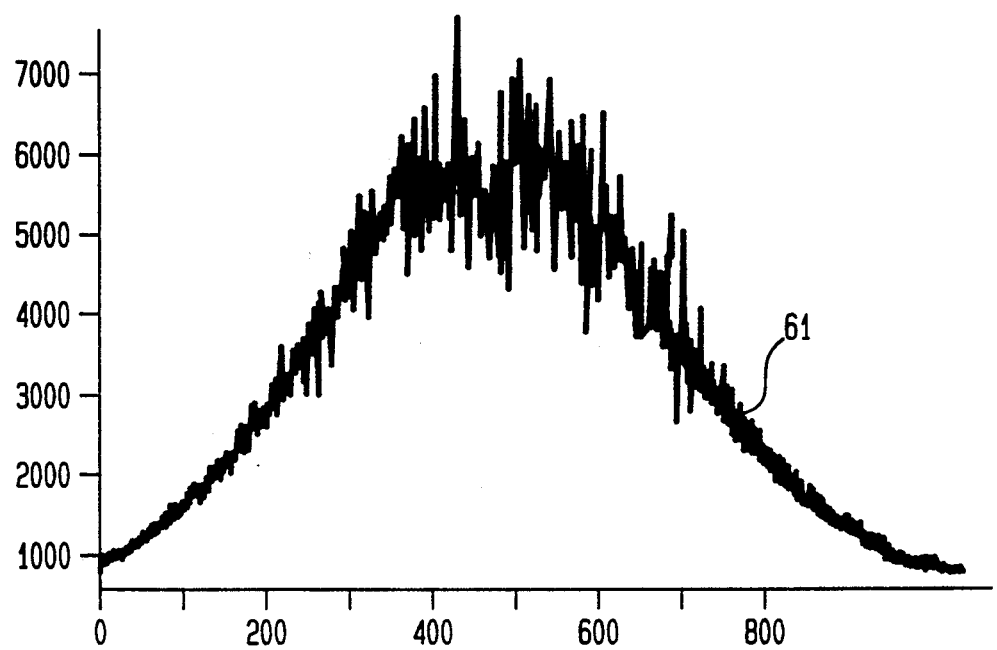
Figure 7C:
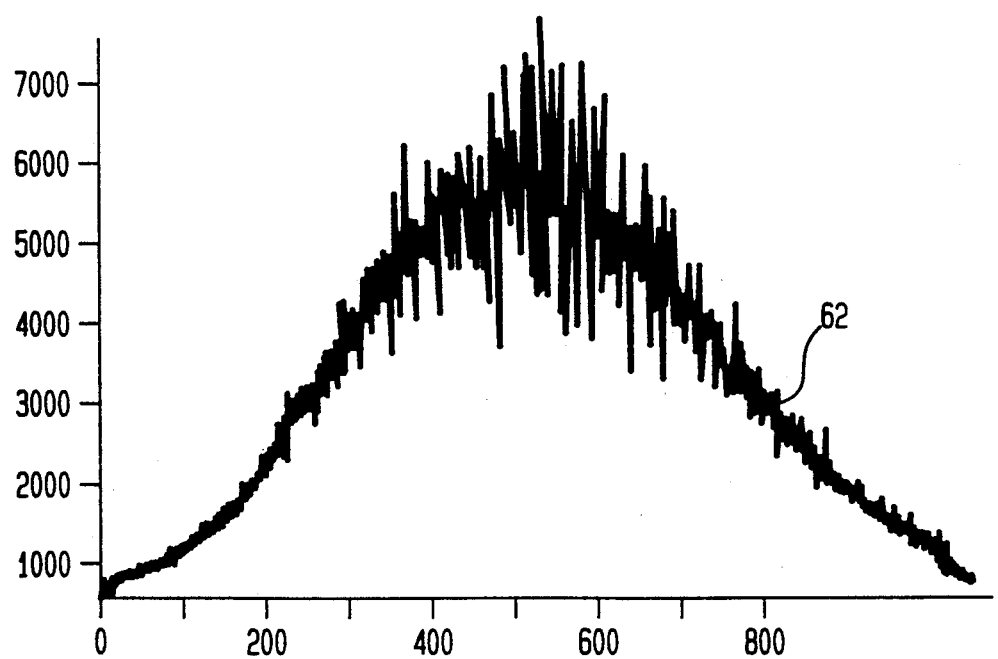

Equations (11)–(14) have been used to provide precise calculations of transmission gratings. Measured interference patterns and calculated interference patterns have been shown to agree within a few percent. A complex pattern produced by a sample can be observed on, for example, a CRT display in apparatus 10. It will be apparent from the foregoing explanation of the optical physics which governs beam propagation that the complex pattern (sometimes called noise), due to irregular width slits, is nothing more than an interference pattern with a perfectly sound physical origin. In FIGS. 6a–6c, there are shown signal patterns 51–53 which were observed on a CRT associated with the signal processor (OMA) 26. In FIG. 6a, the signal pattern 51 corresponds to air alone (no sample). In FIGS. 6b and 6c, the signal patterns 52 and 53 are for a smooth glass slide (sample 22) which provides an optically uniform medium. The change in the pattern 53, produced by a speck of dust, is shown at 54 in FIG. 6c. In FIGS. 7a-7c, interference patterns 60-62 are shown which were observed for black-and-white films. In both FIGS. 6a-6c and FIGS. 7a-7c, the horizontal axis represents the number of image sensors, or pixels (each pixel is 25 μm wide); and the vertical axis represents the photon count (intensity). In comparing the patterns in FIGS. 6b and 6c with the patterns in FIGS. 7a, 7b and 7c, the relatively "clean" response from the glass slide is quite different from the "complex" response from the film in FIGS. 7a-7c. The grainier the film, the larger the "noise", i.e., the interference signal.

The nearly perfect, pure Gaussian display illustrated by the signal pattern (or curve) 51 in FIG. 6a corresponds to "no" specimen (air alone). Thus signal pattern 51 provides the reference or datum for a "perfectly uniform" specimen. By contrast the signal pattern 60 of FIG. 7a, for example, provides immediate, quantitative comparison of the "graininess" and lack of uniformity along a considerable length (e.g., about 25 mm) of a piece of fine-grain, black and white film. The greatly increased graininess or non-uniformity indicated by the signal pattern 60 compared to the signal pattern 51 is immediately apparent. Thus the invention provides a new, extremely fast and very powerful way of quantitatively characterizing a specimen (e.g., a piece of film). The signal patterns of FIGS. 6a, 6b and 6c, and of FIGS. 7a, 7b and 7c are made with "far-field" observation where the detector 24 is located at a relatively great distance from the specimen (the distance between planes "J" and "X" in FIG. 5). By way of example, this distance is 10 cm, which is extremely large relative to the "sizes" of the elements in the specimen. An element such as a "grain" of photographic film may be only a micron or so in diameter. The interferometric patterns of the light waves or photons passing through the specimen and reaching the detector 24 are displayed by the optical multichannel analyzer (OMA) signal processor 26 as the signal patterns of FIGS. 6a, 6b, 6c, and 7a, 7b, 7c, in these "far-field" observations.

Figure 8:
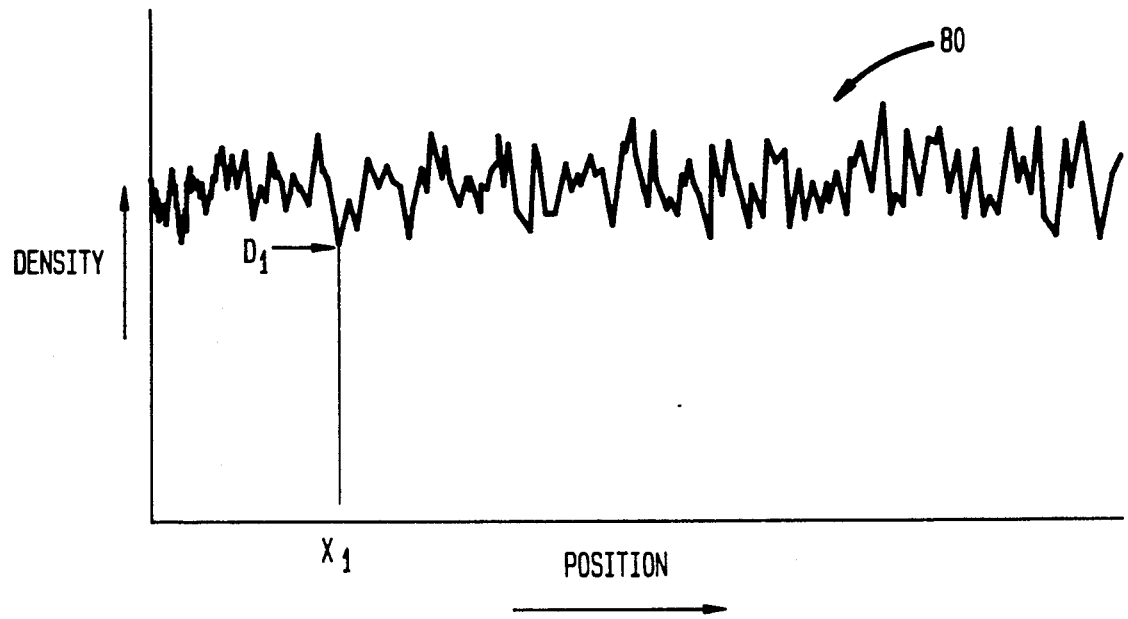
FIG. 8 shows a linearized waveform of density of a piece of black-and-white film.

If desired, the OMA signal processor 26 is capable, in addition, of processing the signal information from the photo detector array 24 to provide conventional measures of density D and standard of deviation sigma ("$\sigma$") from the mean density $\overline{D}$. The original Gaussian signal (representative of a perfectly uniform specimen) is collected as shown by curve 51 in FIG. 6a. Let it be designated as the original signal function $G_1(X)$, where "X" represents the incremental distance along the detector sensors or pixels horizontally and "G" represents the value of intensity I or photon count vertically. This original signal function $G_1(X)$ is stored in a first memory of the OMA 26. The raw data to be analyzed is in the form, for example, of the curve 60 in FIG. 7a, and is designated the signal function $G_2(X)$. This signal function $G_2(X)$ is stored in a second memory of the OMA 26. Taking the ratio of the functions $G_1(X)/G_2(X)$ results in a linear interferometric pattern. This is nothing more than the linearization of the raw data such as in FIG. 7a. Optical density is defined as $D(x) = \log_{10}[G_1(X)/G_2(X)]$. (See, for example, equation 1, p. 39, of the above-identified book entitled "Image Science"). This calculation is done on command in the OMA 26 and provides a displayed function of density such as shown by the "linearized," jagged waveform 80 in FIG. 8 herein. From these data (the linearized waveform 80), the conventional values of mean density $\overline{D}$ and standard deviation $\sigma$ are easily derived. (See, for example, page 619, of the above-identified book "The Theory of The Photographic Process").

Contrary to a conventional microdensitometer, the electro-optical apparatus 10 provided according to the invention has far superior depth of focus, superior sensitivity, much faster data collection, and much greater dynamic range.

As was mentioned previously, in a "near-field" examination of a specimen, a detector such as the photodiode array 24, is located close to a specimen. Such an arrangement is illustrated schematically and not to scale in FIG. 9. Here the detector 24 (shown partly broken away) comprising a linear array of very small (25 μm) individual photo-diodes 90 is located along the line or plane "X" (see also FIG. 5). A specimen 92, by way of example, is an optical-grating having equal lands 94 and slits 95, with equal widths 96 and 97. The specimen 92 lies along a vertical plane "J" (see FIG. 5) and is illuminated by photons from a source "S" (see FIGS. 1a and 1b). The distance from the plane J to the plane X as indicated by distance 98 is small (e.g., a fraction of a millimeter). As illustrated here, each of the photo-diodes 90 is small enough so that at least four diodes respectively span each of the widths 96 and 97 of the lands 94 and the slits 95. For a photo-diode diameter of 25 μm and four photo-diodes 90, the widths 96 and 97 would each be at least 100 μm. With such an arrangement, the output waveform of the detector 24 is a simple "square wave" (digital "on-off" response), with the peaks in intensity representing the slits 95, the troughs of intensity the lands 94, and the spacings of troughs and peaks equaling the respective widths 96 and 97.

Figure 10:
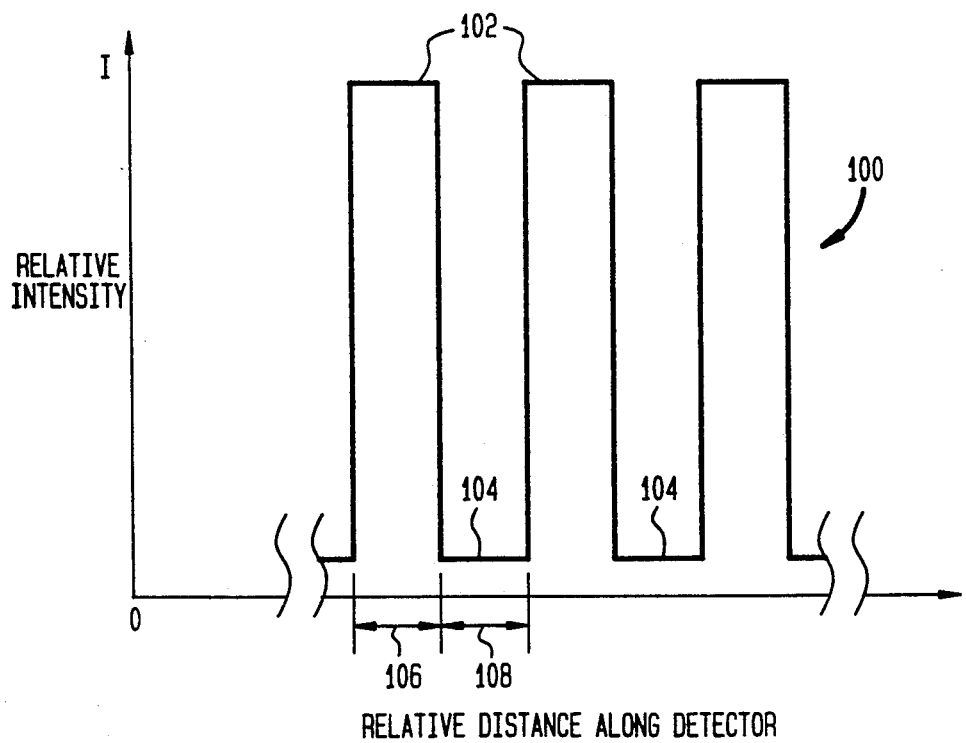
FIG. 10 is a schematic representation of a waveform produced by light waves passing through the specimen to the detector of FIG. 9.
Figure 9:
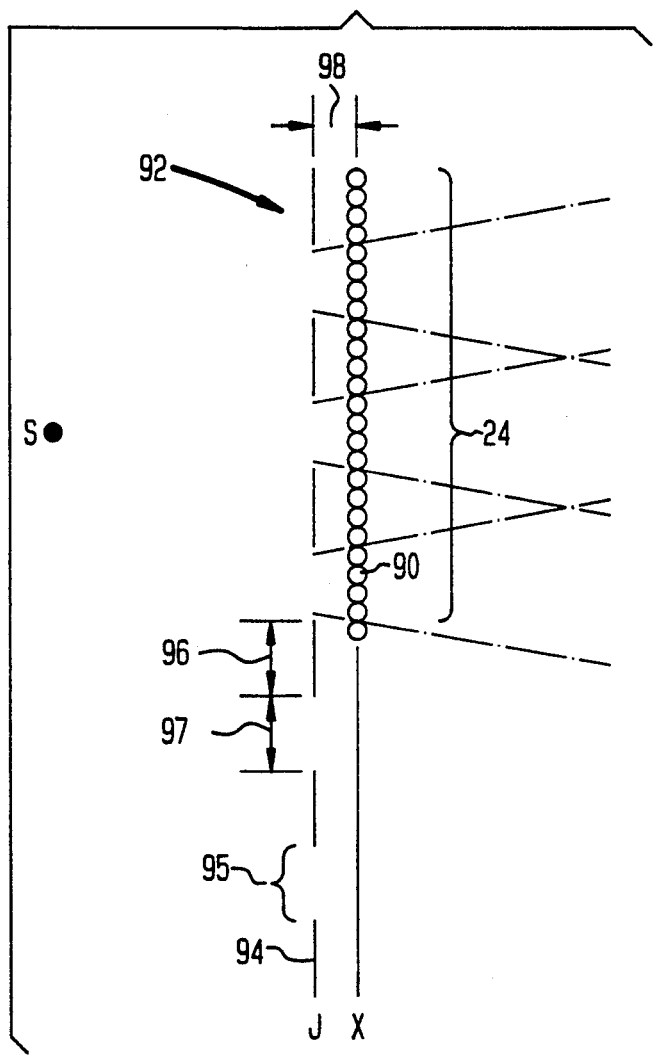
FIG. 9 is a schematic representation of "near-field" examination of a specimen where multiple photo-diodes of a detector span respective fine elements of the specimen.

Referring now to FIG. 10, there is shown, in idealized schematic form and partially broken away, a waveform 100 representative of the "near field" observation of the specimen 92 and the detector 24 as arranged in FIG. 9. The waveform 100 is a simple square-wave (digital on-off response) having "peaks" 102, and "troughs" 104. The widths of the peaks 102 and of the troughs 104 are indicated by distances 106 and 108 respectively. The peaks 102 correspond to the slits 95, and the troughs 104 correspond to the lands 94 of the specimen 92. The widths 106 and 108 correspond respectively to the widths 97 and 96 shown in FIG. 9.

It is to be noted that in the more usual event the elements (e.g., the slits and lands) of the specimen 92 are much smaller than 100 μm. Thus, these elements would not be adequately detected and characterized in "near-field" examination by photo-diodes as large (e.g., 25 μm) as the ones in the detector 24. However, by placing the photo-diodes 90 of the detector 24 at a much greater distance ("far-field" observation) from the specimen 92, the detector 24 "sees" an interferometric pattern of light waves. And from this interferometric pattern the desired information concerning ultra fine elements of the specimen is immediately observed on the OMA 26, as was explained above in conjunction with FIGS. 6a, 6b, and 6c and FIGS. 7a, 7b, and 7c. However, if desired, a "de-interfered" pattern may be derived using the principles of quantum mechanics, as expressed by Equation 13 herein, and discussed in further detail in an article by the invertor Duarte and D. J. Paine, entitled "Quantum Mechanical Description of N-Slit Interference Phenomena", pp. 42-47, in the "Proceedings of the International Conference on Lasers '88," published by STS Press, McLean, Va., 1989. The "de-interfered" pattern is that which is "seen" in "near-field" observation by photo-diodes small enough in diameter so that multiple photo-diodes (e.g., four or more) could span each small element of the specimen (see, for example, FIGS. 9 and 10).

Figure 11:
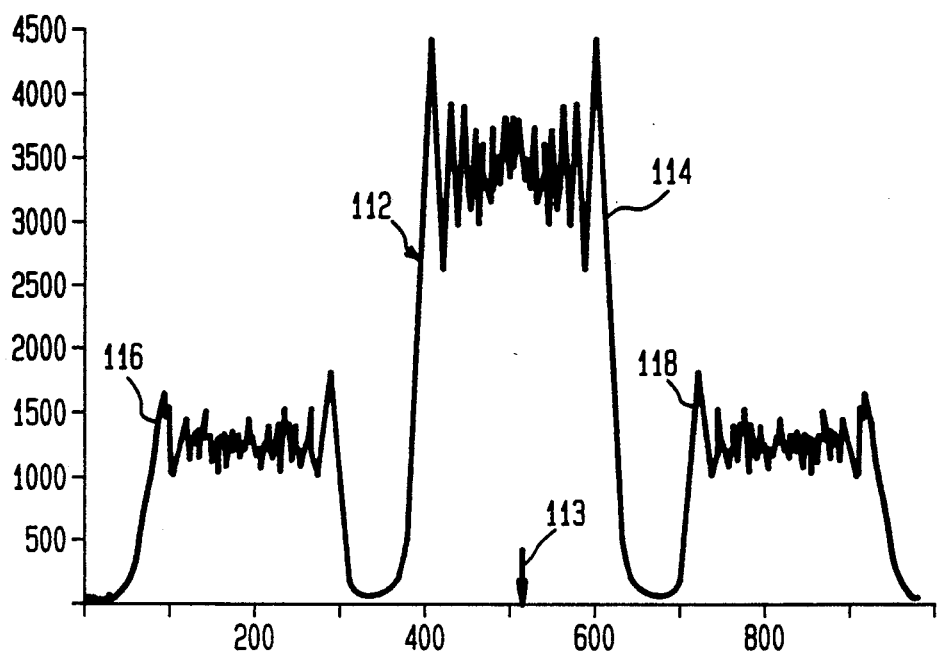
FIG. 11 is an actual display waveform (signal pattern) of a "far-field" observation of a specimen similar to the specimen of FIG. 9.

Referring now to FIG. 11, there is shown a "far-field" observation of a specimen (similar to the specimen 92) displayed as an actual waveform 112 by the OMA 26. The horizontal axis of FIG. 11 is graduated in units from 0 to 1024 which correspond to the individual photo-diodes 92 (see FIG. 9) in the detector 24. A small arrow 113 indicates the mid-point or unit "512" of the detector 24 (having 1024 photo-diodes) along the horizontal axis. The vertical axis of FIG. 11 is graduated in units of light intensity or photon count from 0 to about 4500. These horizontal and vertical axes correspond to the ones shown in FIGS. 6a, b, and c, and FIGS. 7a, b, and c. As seen in FIG. 11 the waveform 112 has a tall central section 114 and two short side sections 116 and 118 which are symmetrical. The specimen actually displayed in FIG. 11 is an optical grating having 67 lands and 67 slits, each 30 microns wide. This specimen has elements (30 μm slits and lands) smaller than but otherwise the same as those of the specimen 92 of FIG. 9. The "far-field" observation distance here in FIG. 11 (specimen to detector, or plane J to plane X of FIG. 5) is 75 cm. In addition to this actual display waveform 112, by using the principles of quantum mechanics as expressed by Equation 13 (given above), it is readily possible also to "compute" a substantially identical interferometric pattern of light waves produced by this specimen when illuminated by a portion (i.e., the central) of a Gaussian beam in accordance with the invention.

Figure 12:
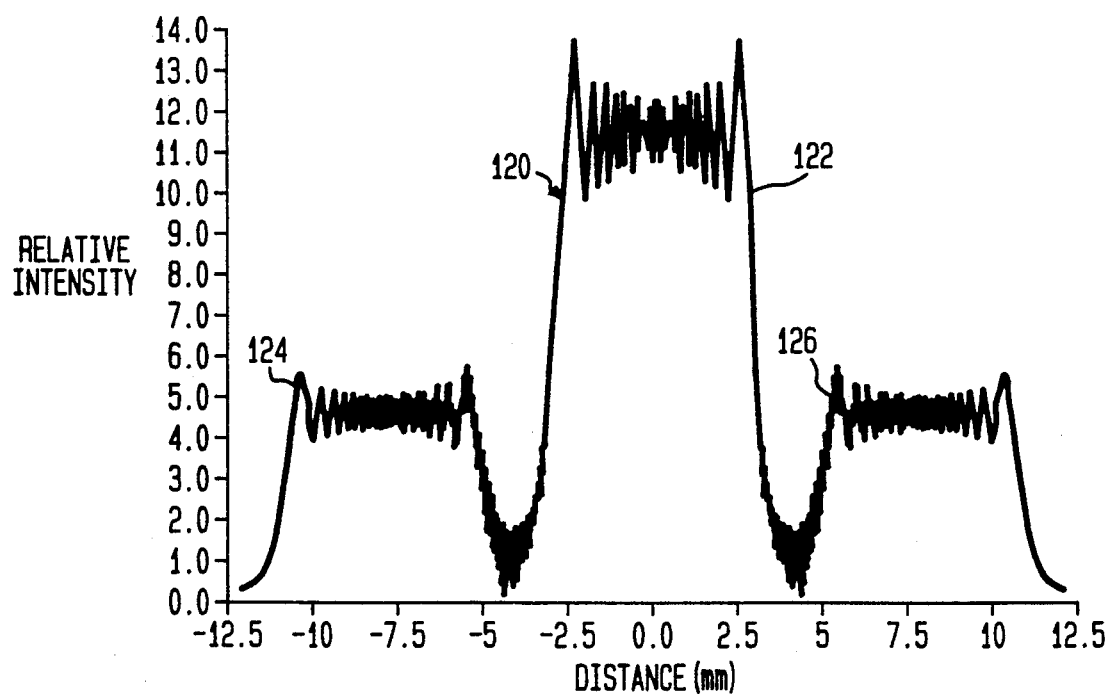
FIG. 12 is a computer-generated waveform of the "far-field" observation of the specimen of FIG. 11 and showing congruity with the actual waveform of FIG. 11.

Referring now to FIG. 12, there is shown a waveform 120 generated by a computer using the principles of quantum mechanics and light wave interference as discussed above in connection with Equations (11)–(14). A person having ordinary skill in mathematics and computer science can readily apply these equations to a given specimen under given conditions. Knowing the wavelength of the light illuminating the specimen, dimensions and number of elements of the specimen, the distance from the specimen to the detector, etc., a waveform (i.e., the waveform 120) is easily generated. Here in FIG. 12 the waveform 120 is computer-generated for the identical conditions of light wavelength, specimen dimensions (i.e., sixty-seven each of 30 micron slits and lands), viewing distance from specimen to detector (i.e., 75 cm) that resulted in the actual display waveform 112 in FIG. 11. It will be noted in FIG. 12 that the waveform 120 has a central portion 122, and two symmetrical side portions 124 and 126. The vertical axis has been normalized into units of relative intensity from 0 to 6.0. The horizontal axis is calibrated in distance in millimeters from a center or zero ("0") position of the detector 24 (about 25 mm total length) to its right (+) and left (−) ends. The zero position corresponds to the position indicated by the arrow 113 in FIG. 11. Aside from minor variations in the computer printout, this waveform 120 is seen to be essentially congruent with the actual display waveform 112 of FIG. 11. The agreement of these waveforms 112 and 120 in the spatial frequency domain (i.e. the horizontal axis) is nearly perfect. This superimposing of the waveforms 112 and 120 proves the validity of the principles of quantum mechanics in interpreting interfering light patterns; it further proves the accuracy of the Equations (11)–(14). In the event that number and dimensions of the elements of the speciment are not precisely known, approximations of these values are iteratively entered into the computer. The various successive waveforms generated by the computer quickly converge to the actual waveform (such as the waveform 112 of FIG. 11) as the dimensional details of the specimen reach their actual values. And, of course, specimens closely similar to an unknown one will already have been characterized and their dimensional details already known. It is thus readily possible to quantatively characterize an unknown specimen by the method and apparatus of the present invention.

After the necessary information (specimen dimensions, viewing distance, etc.) required by the Equations (11)–(14) is entered into the computer, the waveform 120 of FIG. 12 is generated. This waveform 120 is substantially identical to the actual display waveform 112 of FIG. 11 (thus also proving that the data in the computer is correct). The waveform is generated using ideal "error free" grating parameters and propagation parameters. That accounts for the symmetry observed and the clean oscillatory pattern in the ($\pm 1$) orders. Introduction of a small error ($<2\%$) in the grating slit width in the calculations performed via Eqs. 11 to 14 introduces asymmetry and a loss of the oscillatory pattern as observed in the waveform shown in FIG. 11.

The changing to a very small value in the computer of the "viewing distance" (i.e., the distance between plane J and plane X in FIG. 5) in effect "de-interferes" the light pattern from the specimen and makes possible the "viewing" of the specimen at whatever close range is desired. Thus it is possible to examine via a "de-interfered" computer waveform ultra fine details of elements of the specimen, even though these elements are far smaller in width than any available photo-diode, much less a plurality of them. In this way it is possible to "see" elements having dimensions on the order of the wavelength of the light used (e.g., 0.6 micron).

Figure 13:
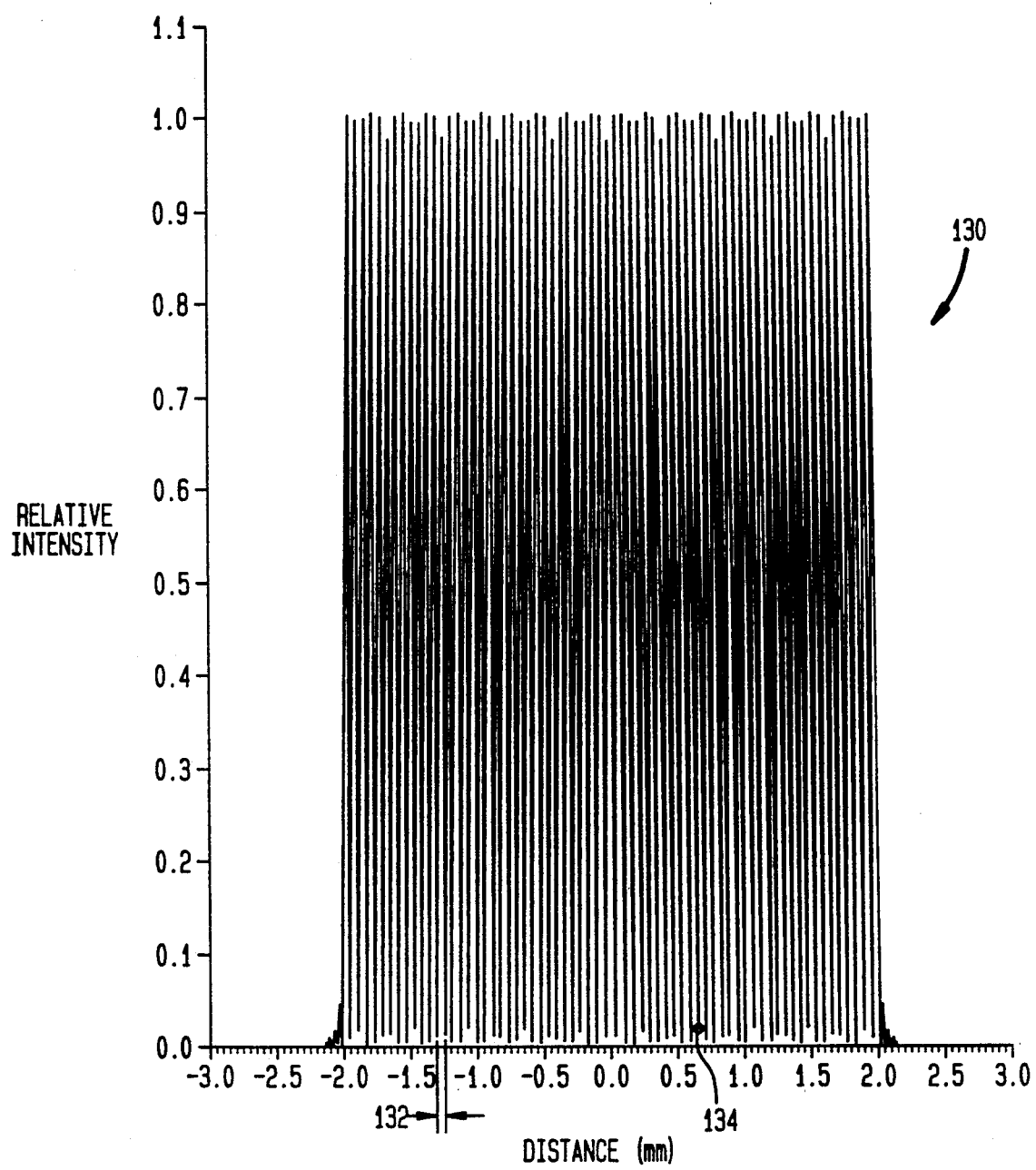
FIG. 13 is a computer-generated waveform showing a "near-field" observation of the specimen of FIG. 12.

Referring now to FIG. 13, there is shown an almost "de-interfered" computer-generated waveform 130. The horizontal axis has been normalized into increments or fine graduations of 50 microns from −3.0 mm to +3.0 mm, and the vertical axis into relative units of intensity from 0 to 1.1. This is a "near-field" pattern of the identical specimen (i.e., an optical grating having sixty-seven each of 30 μm lands and slits) which produces the "far-field" patterns shown in FIG. 11 as the actual display waveform 112, and in FIG. 12 as the computer generated waveform 120. Here in FIG. 13, the "viewing distance" is arbitrarily chosen at 1.5 mm instead of the 75 cm distance of FIGS. 11 and 12. It will be noted that in FIG. 13 there are sixty-seven (67) fine gaps indicated at 132 which correspond to the combined slits and lands of the specimen (60 μm combined widths). This is because there is still some light "fringing" with the fine details of this specimen at the 1.5 mm viewing distance. The waveform 130 is seen to span slightly more than 4 mm. The combined length of 67 lands and 67 slits of 30 μm each is 4020 microns (slightly more than 4 mm). If a viewing distance substantially closer than the 1.5 mm used here (e.g., 0.1 mm) were entered into the computer, the sharp "points" indicated at 134 in FIG. 13 would spread out to become flat "lands" equal in width to the slits, giving a combined width of a land and a slit of 60 μm. In effect, it is possible by choosing a "viewing distance" close enough, to simulate in the computer an arrangement such as shown in FIG. 9 where multiple photo-diodes 90 cover each of the lands 94 and the slits 95. The computer display for the particular specimen of FIGS. 11, 12 and 13 (at a close enough viewing distance) will provide information similar to the simple digital type waveform 100 of FIG. 10. The distance 106 in FIG. 10 corresponds to a slit width (e.g., 30 μm) and the distance 108 corresponds to an equal land width.

It should be noted that the fine elements of a specimen, such as the specimen 92 in FIG. 9, are not limited to equal or uniform "slits" and "lands", or to a particular number or pattern of elements. The generalized equations of light interference and the physics of quantum mechanics apply to the elements of any specimen which provides light interference patterns. As explained above, the method and apparatus of the present invention are useable in both "far-field" and "near-field" examination of various specimens.

Figure 14:
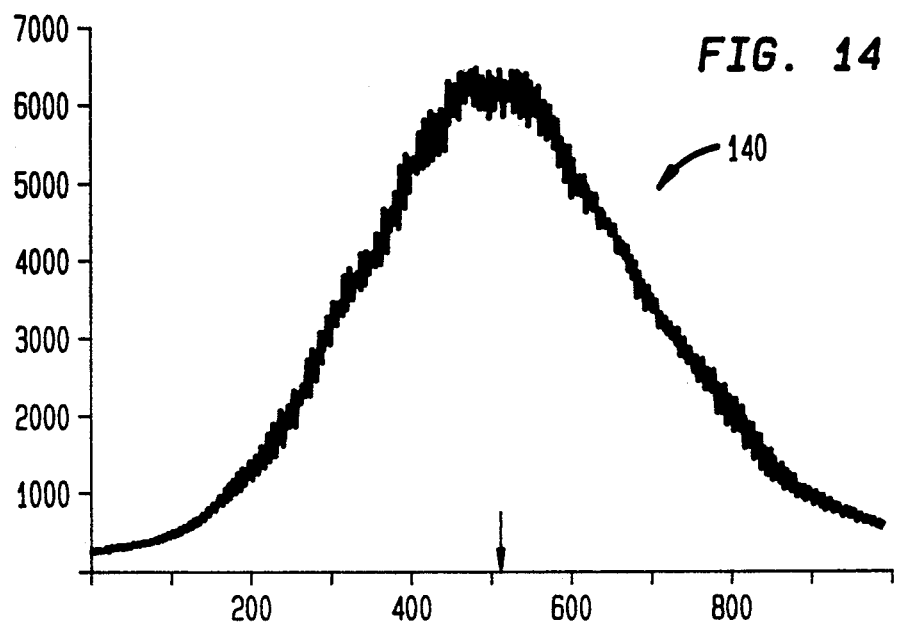
FIG. 14 is an actual display waveform (interference pattern) showing non-uniformity of a piece of clear substrate of photographic film.

Referring now to FIG. 14, there is shown a waveform 140 which is an actual signal response of the detector 24 displayed on the CRT of the OMA 26. Waveform 140 is the interferometric pattern of light waves produced by a "clear" thin piece of photographic film substrate. The viewing distance from this piece of film to the detector 24 is 10 cm. The horizontal and vertical axes are here calibrated the same as in FIGS. 6a, b, c, FIGS. 7a, b, c, and FIG. 11. It is to be noted that the waveform 140 in FIG. 14 shows a noticeably larger amount of "interference" than the waveform (signal response) 52 of FIG. 6b. The latter waveform 52 shows the interference pattern produced by a clear, smooth, optically uniform glass slide (sample 22). A conventional microdensitometer is not capable of detecting, much less quantifying the non-uniformity of the piece of clear quality film substrate shown by the waveform 140 of FIG. 14. This is partly because the slightly non-uniform structure of the piece of film substrate occurs throughout its thickness. Also, inherent noise problems in conventional microdensitometers prevent the measurement of these low-level effects of the non-uniform structure of the substrate. This film thickness is typically many times greater than the depth of focus of a conventional microdensitometer, as explained previously. However, the non-uniformity of the piece of photographic film substrate (without a photographic emulsion on its surface) is immediately evident in the waveform 140 of FIG. 14. Using the method and apparatus of the invention, polymeric film substrate material can now be uniquely quantified as to its microscopic uniformity and quality.

Figure 15:
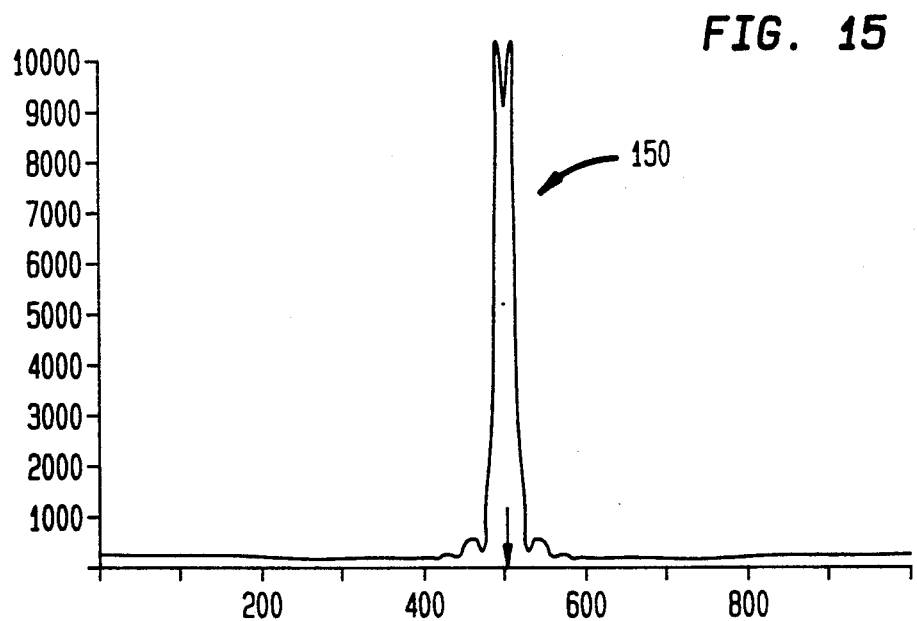
FIG. 15 is a display waveform (interference pattern) showing a micro-defect in a high optical density metal film.

Referring now to FIG. 15, there is shown a waveform 150 which is an actual signal response generated by the detector 24 and displayed on the CRT of the OMA 26. This waveform 150 is the diffraction pattern of light waves produced by a micro-defect in a high optical density metal film. Here a high quality and expensive neutral density filter (optical density of $10^4$ in linear units) is found to have a microhole which causes considerable divergence and a diffraction pattern of light waves on the detector 24 (which has a length of about 25 mm). It would be a very time consuming task to find the microhole using a conventional microdensitometer, which, as explained above, must search a small (e.g., 48 μm) spot of the specimen a step at a time over a very large area. Here in FIG. 15 however, the microhole is immediately evident from the waveform 150 on the OMA 26. The vertical and horizontal axes of FIG. 15 are calibrated the same as in FIG. 14. The viewing distance is likewise 10 cm.

It is to be understood that the apparatus and method described herein are illustrative of the general principles of the invention. Modifications may readily be devised by those skilled in the art without departing from the spirit and scope of the invention. For example an OMA signal processor other than the one described, and a photo-detector employing more or fewer individual photo-diodes may be used. The invention is not limited to a particular arrangement of optical elements, or to particular "viewing distances". It is not limited to a given light beam width, or to a wavelength of light in the visible spectrum. Quantative characterization of a specimen may be achieved by "far-field" observation alone, but the invention is not limited solely to this mode.

What is claimed is:

1. Electro-optical apparatus comprising:
   means for generating a wide, thin substantially pure Gaussian beam of light;
   means for holding a specimen to be examined in the light beam at a first location; and
   detector means at a second location spaced from the first location for receiving a pattern of interfering light waves coming from the specimen, and for generating electrical signals in accordance with the pattern of interfering light waves.

2. The apparatus of claim 1 wherein the detector means is a linear array of a multitude of very small photo-diodes, the length of the detector means being approximately equal to the width of the Gaussian beam.

3. The apparatus of claim 2 in further combination with an optical multichannel analyzer (OMA), the OMA being connected to the photo-diodes of the detector means for producing an interferometric waveform display such that ultra fine details of elements along a length of the specimen can be characterized.

4. The apparatus of claim 1 wherein the means for generating comprises a laser emitting a substantially pure Gaussian beam of light at a selected wavelength.

5. The apparatus of claim 4 wherein the wavelength of the light is about 0.6 micron, and the laser beam is expanded laterally from a diameter of a fraction of a millimeter to a width of many tens of millimeters.

6. The apparatus of claim 4 wherein the specimen location and the location of the detector means are separated by some centimeters in distance.

7. The apparatus of claim 3 wherein the OMA selectively generates a linearized display of the density of a specimen having non-uniformities in it as compared to a perfectly uniform specimen.

8. Electro-optical apparatus comprising:
   laser and beam expander means for generating a wide, thin substantially pure Gaussian beam of light;
   means for holding a specimen to be examined in the light beam at a first location; and
   an array of photo-detectors at a second location spaced from the first location for receiving a pattern of interfering light waves coming from the specimen, the photo-detectors being capable of generating electrical signals in accordance with the pattern of interfering light waves, such that ultra fine elements of the specimen are characterized even though an individual photo-detector is substantially larger than an individual element of the specimen.

9. The apparatus of claim 8 wherein the Gaussian beam has a great depth of focus at the first location, such that elements of a relatively thick specimen such as a piece of polymeric substrate can be characterized as to their degree of non-uniformity throughout the thickness of the specimen.

10. The apparatus of claim 8 wherein the Gaussian beam has a width at the specimen location very much larger than a spot of about 50 μm such that a length of a specimen can be examined and characterized simultaneously in a relatively short time period.

11. Apparatus for measuring the optical characteristics of a sample located along an optical axis, said apparatus comprising:
 a coherent light source for producing a beam of light along said optical axis;
 optical means for receiving said beam of light from said light source and for producing a narrow and elongated beam on said sample at a focal plane of said optical means; and
 means for detecting light transmitted through said sample and for producing an electrical signal proportional thereto.

12. The apparatus of claim 11 wherein said detecting and producing means comprises means for producing an interference pattern indicative of the material of said sample.

13. The apparatus of claim 11 wherein said light source in a HeNe laser.

14. The apparatus of claim 11 wherein said optical means comprises a telescope.

15. The apparatus of claim 11 wherein said optical means comprises a multiple-prism beam expander.

16. Apparatus ad defined in claim 15, wherein said beam expander comprises a plurality of right-angle prisms.

17. The apparatus of claim 11 wherein said detector means comprises a linear photo-diode array.

18. The apparatus of claim 11 wherein said narrow and elongated beam is at between about 35 mm and about 50 mm along one dimension thereof.

19. A system for optically examining and characterizing ultra small details of elements of a specimen comprising:
 laser means for generating a substantially pure Gaussian narrow beam of light at a desired wavelength;
 beam expander means for expanding the Gaussian beam into a much wider beam of light and for projecting it along an optical axis;
 means for holding a specimen to be examined at a first location along the optical axis of the wider light beam; and
 light detector means for detecting the pattern of light waves from a specimen and for generating electrical signals therefrom, said detector means having a width commensurate with the width of the wider light beam, the detector means being located along the optical axis at a suitable distance from the first location such that ultra small details of elements of a specimen are indicated by the light waves from the specimen are characterized in the form of electrical signals generated by the detector means.

20. The system of claim 19 wherein the detector means comprises a large number of small photo-diodes in an array having a width about equal to the width of the wider light beam such that individual details of elements of a specimen much smaller than an individual photo-diode can be characterized by the electrical signals.

21. The system of claim 20 in further combination with an optical multichannel analyzer (OMA) coupled to the detector means for displaying a waveform showing the degree of non-uniformity of a specimen compared to a uniform one.

22. The system of claim 21 wherein the detector means is located far enough away from the specimen location to see or detect an interferometric pattern of light waves or photons from the specimen such that elements of the specimen having a size of the order of the wavelength of the beam of light are characterized.

23. The system of claim 22 wherein the wavelength of the beam of light is in the visible spectrum.

24. A method of optically examining a specimen by interferometric patterns of light comprising the steps of:
 generating a wide substantially pure Gaussian beam of light;
 illuminating a specimen with the beam of light to produce a "far-field" interferometric pattern of light waves at a "far-field" distance from the specimen; and
 detecting and converting into electrical signals the "far-field" interferometric pattern of light waves to characterize ultra fine details of the specimen over a part of its width.

25. The method of claim 24 further comprising the step of using the principles of quantum mechanics to generate for a "near-field" distance a "near field" characterization of the specimen.

26. The method of claim 25 wherein the "near field" characterization of the specimen is a computer-generated waveform, the "near-field" distance being very much shorter than the "far-field" distance.

27. The method of claim 24 further comprising the step of displaying on an optical multichannel analyzer (OMA) the electrical signals to produce a waveform characterizing the specimen.

28. The method of claim 27 further comprising the step of producing in the OMA a linearized display of density of the specimen.

29. A method of examining a specimen by patterns of light comprising the steps of:
 generating a substantially pure Gaussian beam of light;
 expanding the beam of light into a very much wider beam of light having substantially parallel rays;
 illuminating a specimen with the beam of light to produce a "far-field" pattern of interfering light waves; and
 converting into electrical signals the "far-field" pattern of light waves to characterize details of the specimen such that details having sizes on the order of the wavelength of the light beam are characterized.

30. The method of claim 29 further comprising the step of computer-generating a computer waveform corresponding to the "far-field" interferometric pattern of converted electrical signals.

31. The method of claim 30 further comprising the step of computer-generating a "near-field" computer waveform corresponding to the "far-field" computer waveform.

32. Apparatus comprising:
 means for generating a Gaussian beam of light having a thickness which is substantially smaller than the width thereof;
 means for directing the beam of light so as to cause it to impinge upon an object whose physical characteristics are to be determined; and
 detector means for directing interferometric light waves from the object and for generating electrical signals representative of the physical structure of the object.

* * * * *

UNITED STATES PATENT AND TRADEMARK OFFICE
CERTIFICATE OF CORRECTION

PATENT NO. : 5,255,069

DATED : October 19, 1993

INVENTOR(S) : Francisco J. Duarte

It is certified that error appears in the above-indentified patent and that said Letters Patent is hereby corrected as shown below:

Columns 7-8, equation 6 should be changed as follows

$$\begin{bmatrix} A & B \\ C & D \end{bmatrix} =$$

$$\begin{bmatrix} \prod_{m=1}^{r} k_m & (\ell/n)\left[\prod_{m=1}^{r} k_m \sum_{m=1}^{r} \left(\prod_{j=1}^{m} k_j\right)^{-2}\right] + \left[\prod_{m=1}^{r} k_m \sum_{m=1}^{r-1} \left(\prod_{j=1}^{m} k_j\right)^{-2}\right] D \\ 0 & \left(\prod_{m}^{r} k_m\right)^{-1} \end{bmatrix}$$

Eq.(6)

UNITED STATES PATENT AND TRADEMARK OFFICE
CERTIFICATE OF CORRECTION

PATENT NO. : 5,255,069  
DATED : October 19, 1993  
INVENTOR(S) : Francisco J. Duarte Page 2 of 2

It is certified that error appears in the above-indentified patent and that said Letters Patent is hereby corrected as shown below:

Column 7, line 14, after "where" insert -- ℓ --

Signed and Sealed this

Fourteenth Day of June, 1994

Attest:

BRUCE LEHMAN

Attesting Officer  Commissioner of Patents and Trademarks